US009730578B2

(12) United States Patent
Lai (10) Patent No.: US 9,730,578 B2
(45) Date of Patent: *Aug. 15, 2017

(54) SELF GUIDED SUBJECTIVE REFRACTION INSTRUMENTS AND METHODS

(71) Applicant: Shui T Lai, Windermere, FL (US)

(72) Inventor: Shui T Lai, Windermere, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 15/218,079

(22) Filed: Jul. 25, 2016

(65) Prior Publication Data

US 2017/0100031 A1   Apr. 13, 2017

Related U.S. Application Data

(63) Continuation of application No. 14/631,318, filed on Feb. 25, 2015, now Pat. No. 9,408,533, which is a continuation of application No. 14/158,926, filed on Jan. 20, 2014, now Pat. No. 8,967,801, which is a continuation of application No. 12/948,736, filed on Nov. 17, 2010, now Pat. No. 8,632,184.

(51) Int. Cl.
*A61B 3/10* (2006.01)
*A61B 3/00* (2006.01)
*A61B 3/032* (2006.01)
*A61B 3/028* (2006.01)
*A61B 3/036* (2006.01)
*A61B 3/04* (2006.01)

(52) U.S. Cl.
CPC ........ *A61B 3/0033* (2013.01); *A61B 3/0041* (2013.01); *A61B 3/0091* (2013.01); *A61B 3/0285* (2013.01); *A61B 3/032* (2013.01); *A61B 3/036* (2013.01); *A61B 3/04* (2013.01)

(58) Field of Classification Search
CPC ........ A61B 3/103; A61B 13/005; A61B 3/113

USPC ................ 351/204–205, 200, 210
See application file for complete search history.

(56) References Cited

U.S. PATENT DOCUMENTS 3,067,647 A   12/1962   Sato
4,477,158 A   10/1984   Pollock et al.
4,601,545 A   7/1986   Kern
4,953,956 A   9/1990   Carpenter
(Continued)

FOREIGN PATENT DOCUMENTS

CN   101721195 A   6/2010
DE   102004041325 A1   3/2006
(Continued)

OTHER PUBLICATIONS

PCT Notification of Transmittal of the International Search Report and the Written Opinion of the International Searching Authority, or the Declaration, for PCT Application No. PCT/US2011/061082, report dated Mar. 6, 2012, 14 pages.
(Continued)

*Primary Examiner* — Dawayne A Pinkney
(74) *Attorney, Agent, or Firm* — SF Bay Area Patents, LLC; Andrew V. Smith (57) ABSTRACT

A refraction device determines a refraction end point to provide corrective optics for a test subject. The device includes an adjustable optical system providing corrective optics to the test subject and an adjustable viewing target disposed along an optical path such as to be viewable through the adjustable optical system by a test subject. The adjustable viewing target includes a directional indicator linked synchronously to at least two choices of corrective optics presented to the test subject.

39 Claims, 4 Drawing Sheets

(56) References Cited

U.S. PATENT DOCUMENTS

| | | | |
|---|---|---|---|
| 5,880,814 | A | 3/1999 | McKnight et al. |
| 5,929,972 | A | 7/1999 | Hutchinson |
| 7,461,938 | B2 | 12/2008 | Lai |
| 7,699,471 | B2 | 4/2010 | Lai |
| 7,726,811 | B2 | 6/2010 | Lai |
| 8,632,183 | B2 | 1/2014 | Lai |
| 8,632,184 | B2 | 1/2014 | Lai |
| 8,950,865 | B2 | 2/2015 | Lai |
| 8,967,801 | B2 | 3/2015 | Lai |
| 9,408,533 | B2 | 8/2016 | Lai |
| 2004/0105073 | A1 | 6/2004 | Maddalena et al. |
| 2005/0083485 | A1 | 4/2005 | Toshima et al. |
| 2005/0174535 | A1 | 8/2005 | Lai et al. |
| 2006/0227289 | A1 | 10/2006 | Hasegawa |
| 2008/0018857 | A1 | 1/2008 | Koppany |
| 2010/0007850 | A1 | 1/2010 | Aggarwala |
| 2010/0128223 | A1 | 5/2010 | Blumenthal et al. |
| 2012/0120369 | A1 | 5/2012 | Lai |
| 2012/0120370 | A1 | 5/2012 | Lai |
| 2014/0340646 | A1 | 11/2014 | Lai |

FOREIGN PATENT DOCUMENTS

| | | |
|---|---|---|
| EP | 2005878 A1 | 12/2008 |
| EP | 2640256 A4 | 9/2015 |
| JP | 2000-079096 A | 3/2000 |
| UA | 67919 A | 7/2004 |
| WO | 2006092804 A2 | 9/2006 |
| WO | 2012068311 A1 | 5/2012 |
| WO | 2012068312 A1 | 5/2012 |

OTHER PUBLICATIONS

PCT Notification of Transmittal of International Preliminary Report on Patentability Chapter I, including International Preliminary Report on Patentability Chapter I-IB-373, for PCT Application No. PCT/US2011/061082, report dated May 21, 2013, 10 pages.

Non-Final Rejection dated Feb. 13, 2013, for U.S. Appl. No. 12/948,736, filed Nov. 17, 2010.

Final Rejection dated Oct. 23, 2013, for U.S. Appl. No. 12/948,736, filed Nov. 17, 2010.

Notice of Allowance dated Dec. 6, 2013, for U.S. Appl. No. 12/948,736, filed Nov. 17, 2010.

PCT Notification of Transmittal of the International Search Report and the Written Opinion of the International Searching Authority, or the Declaration, for PCT Application No. PCT/US2011/061080, report dated Apr. 17, 2012, 9 pages.

PCT Notification of Transmittal of International Preliminary Report on Patentability Chapter I, including International Preliminary Report on Patentability Chapter I-IB-373, for PCT Application No. PCT/US2011/061080, report dated May 21, 2013, 8 pages.

Non-Final Rejection dated Jan. 17, 2013, for U.S. Appl. No. 12/947,694, filed Nov. 16, 2010.

Final Rejection dated Oct. 23, 2013, for U.S. Appl. No. 12/947,694, filed Nov. 16, 2010.

Notice of Allowance dated Nov. 8, 2013, for U.S. Appl. No. 12/947,694, filed Nov. 16, 2010.

EPO Communication regarding the transmission of the European search report, European search opinion, and Supplementary European search report, for European patent application No. 11841072.9, report dated Aug. 6, 2015, 7 pages.

Notice of Allowance dated Sep. 26, 2014, for U.S. Appl. No. 14/158,926, filed Jan. 20, 2014.

Supplemental Notice of Allowance dated Jan. 27, 2015, for U.S. Appl. No. 14/158,926, filed Jan. 20, 2014.

Machine-generated translation of CN 101721195 A, "Remote self-help refraction system for presbyopic glasses and method thereof," published on Jun. 9, 2010, 6 pages. Retrieved from URL:https://www.google.com/patents/CN101721195A?cl=en.

EPO Communication regarding the transmission of the European search report, European search opinion, and Supplementary European search report, for European patent application No. 11842072.8, report dated Aug. 5, 2015, 5 pages.

Machine-generated translation of DE 102004041325 A1, "Subjective corrective lens assignment and vision determination method using appropriate fan-shaped test chart, involves determining visual acuity of human eyes using electronic data processor, and assigning corrective lens for examined eyes," published on Mar. 2, 2006, 3 pages. Retrieved from URL:https://www.google.com/patents/DE102004041325A1?cl=en.

Patent Abstracts of Japan, Publication No. 2000079096 A, Date of publication of application: Mar. 21, 2000, for "OPTOMETER." 1 page.

Machine-generated translation of JP 2000-079096 A, "OPTOMETER," published on Mar. 21, 2000, 4 pages. Retrieved from URL:https://patentspope.wipo.int/search/enidetail.jsf?docId=JP66316858&recNum=2&maxRec=2&office=&prevFilter=&sortOption=Pub+Date+Desc&queryString=JP2000079096&tab=PCTDescription.

Non-Final Rejection dated Oct. 2, 2015, for U.S. Appl. No. 14/631,318, filed Feb. 25, 2015.

Notice of Allowance dated Oct. 2, 2015, for U.S. Appl. No. 14/631,318, filed Feb. 25, 2015.

SELF GUIDED SUBJECTIVE REFRACTION INSTRUMENTS AND METHODS

PRIORITY

This application is a Continuation of U.S. patent application Ser. No. 14/631,318, filed Feb. 25, 2015, now U.S. Pat. No. 9,408,533; which is a Continuation of U.S. patent application Ser. No. 14/158,926, filed Jan. 20, 2014, now U.S. Pat. No. 8,967,801; which is a Continuation of U.S. patent application Ser. No. 12/948,736, filed Nov. 17, 2010, now U.S. Pat. No. 8,632,184; and is incorporated herein by reference.

BACKGROUND OF THE INVENTION

Manifested refraction remains one of the most reliable methods of arriving at a prescription to correct refractive errors, whether it is used for preparing prescription eyeglasses or contact lenses, or for laser surgery. However, the current refraction methods have many challenges, including a steep learning curve, and difficulty in mastering the art, and it typically involves months of practice to learn to produce good prescriptions. Another challenge is that it involves patient participation. The end point comes after many steps, each involving a forced answer from the patient. The accuracy of each of the answers determines whether the entire eye test is moving in the correct direction. A wrong answer may lead the exam down a wrong path. In the course of the refraction process, a patient may often ask to repeat the choices presented to them, because they are not sure or can't decide. Repeating tests and steps in tests often is done to ensure accurate results. The repeated questioning causes anxiety on the part of the patient, and the lengthening of the eye exam time. Hence a refraction method that can reduce or eliminate patient's requests for repeat presentations would be desirable and beneficial.

Refraction Testing

The most often asked question in a phoropter refraction test is "Is it better one, or better two", while the conductor of the refraction test flips the lenses to present choice one versus choice two. Once an answer is given by the test subject, the conductor has to know what to do in the next move. The knowing of the next move takes training, and it is a somewhat long and steep learning curve. In an example of a test using a phoropter, the operator or the conductor of the test would ask "is it better one (e.g., at −1.75 D) or better two (e.g., at −2.0 D)?" First, the patient decides which presentation looks better. He or she memorizes presentation one when comparing it to presentation two. He or she may ask: "Can you show me again?" If an answer is finally given, the operator then selects which lens is to be presented next, i.e., from typically extensive training and practice.

In the current state of the art in refraction technology, there are auto refractors, retinal scopes, and wavefront aberrometers. None has the reliability and accuracy that is comparable to a traditional phoropter. Therefore, the outcomes of most objective refraction instrument tests are used as starting points, and not as acceptable final refraction results. Hence it would be a breakthrough for any refraction technology to produce results comparable or superior to those of the phoropter, and even more so if that technology can be conducted by patients with a minimum or no supervision.

A self-guided refraction test would also produce huge economic advantages. As it is said, the mastering of phoropter refraction is difficult, and involves months or years to perfect it. A large proportion of refraction tests are currently performed by ophthalmologists or optometrists. These medical professionals typically earn a high pay. Therefore, the cost of refraction may be reduced substantially if it is performed by a technician, under the supervision of an eye care professional. The cost may be further reduced, if the test is performed by the patient under the supervision of a technician or eye care professional.

A separate computer input panel may be provided for the operator to control the test. That is, a separate person from the test administrator may be enlisted to run the program and use the panel to choose the next move in the refraction procedure. It is desired to have a self-guided refraction test process.

Over-Minusing

It is also desired to reduce or eliminate over-minus conditions. In a population, those persons under the age of 45 generally have eyes with adjustable focal power, or accommodation. During a typical eye exam, a Snellen eye chart viewing target is presented for the patient as the viewing target. Such an eye chart, consisting of letters of various sizes, typically arranged in a series of rows, is widely used in an eye exam to guide the doctor to find the optimal lens setting in a device called a phoropter. A patient's ability to read certain lines determines a measure of the level of quality vision, or visual acuity. One challenge during a refraction process is that a patient may often choose a higher negative power, because the letters appear darker and tighter, and are therefore perceived as being "sharper". A 14 year old patient may have up to 8 diopters of accommodation power. This over-minusing can continue to lead the process down deeper and deeper into the minus power territory.

There is an existing mitigation method. It involves the patient "earning" the extra minus power unless the visual acuity is improved at the more minus power setting. However, this method sometimes fails when the patient adapts to the more minus power and rejects the less minus due to the locking mechanism of the muscle of the eye, that won't release the tension. In other words, once a patient is over-minus, it is difficult to reverse it. Wearing over-minus eyeglasses, patients tend to complain about headaches and dizziness, leading to a redoing or a remaking of the lens prescription, which costs lost time and unhappy patients. Hence it is desirable to provide a method that can reduce or eliminate over-minus in a refraction process.

Hence, it is desired to provide a refraction instrument and refraction method that reduces or eliminates the over minusing, and is relatively easy to learn and easy to perform. It is desired that the instructions for such refraction procedure be simple and understandable by most people who are capable of verbal communication, literate or illiterate, and that the instructions are universally applicable to all age groups, and without causing confusion.

DETAILED DESCRIPTIONS OF THE EMBODIMENTS

A refraction device is provided for determining a visual acuity and providing corrective optics for a test subject. The device includes an adjustable optical system and an adjustable viewing target disposed along an optical path such as to be viewable through the adjustable optical system by a test subject. The adjustable viewing target includes a directional indicator linked synchronously to at least two choices of corrective optics presented to the test subject.

The device may include an input device configured to be controlled by the test subject to indicate a direction suggested by the directional indicator for selecting between the at least two choices of corrective optics. The direction suggested by the directional indicator corresponds to a corrective optics choice as presented to the test subject by the viewing target.

The adjustable viewing target may be adjustable to at least two configurations each uniquely indicative of one of the choices of corrective optics.

The directional indicator may include a relatively light dot inside a dark area, or vice-versa, a bar or other in-plane rotationally asymmetric polygon, an arrow, a line, or another in-plane rotationally-dependent object, or combinations thereof. The directional indicator may be configured to be displayed to the test subject in at least two configurations each uniquely indicative of one of the choices of corrective optics. The directional indicator may include a white dot inside a black area, such that the white dot is movable to certain positions each demonstrating a certain direction corresponding to one of the choices of corrective optics.

The device may also include a machine coupled with a display and configured to adjust the viewing target on the display during a visual acuity measurement of a test subject. A calculator or look-up table, or both, may be used to determine the visual acuity of the test subject based on the visual acuity measurement.

To prevent accommodation, the device may be configured to display for 0.4 seconds or less a first corrective optic having more minus sphere than a second corrective optic to be displayed of the at least two choices of corrective optics. The second corrective optic may be displayed after the first corrective optic for longer than the first corrective optic, after which the display of the first and second corrective optics may be repeated one or more times during the visual acuity measurement.

A refraction method is also provided for determining a visual acuity and providing corrective optics for a test subject. An optical system may be adjusted to a first configuration for the test subject to view through a first corrective optic a viewing target including a first directional indicator. The optical system may then be adjusted to a second configuration for the test subject to view through a second corrective optic the viewing target including a second directional indicator. A directional input is received, in accordance with the first or second directional indicator, from the test subject uniquely indicating a choice of one of the first and second corrective optics. Based on the choice, one or more further configurations may be selected for the test subject to view through one or more further corrective optics for the test subject to choose until a prescriptive recommendation is determined. The prescriptive recommendation may be communicated based on the choices.

The receiving of the directional input may include receiving a signal from an input device controlled by the test subject to indicate a direction suggested by the directional indicator for selecting between the first and second corrective optics. The method may include presenting to the test subject the choice between the first and second corrective optics in accordance with unique directions each suggested by the directional indicator as corresponding to one of the first and second corrective optics.

The directional indicator of the viewing target may be adjusted to at least two configurations each uniquely indicative of one of the choices of corrective optics.

The directional indicator may include a relatively light dot inside a dark area, or vice-versa, a bar or other in-plane rotationally asymmetric polygon, an arrow, a line, or another in-plane rotationally-dependent object, or combinations thereof. The directional indicator may be configured to be displayed to the test subject in at least two configurations each uniquely indicative of one of the choices of corrective optics. The directional indicator may include a white dot inside a black area, such that the white dot is movable to certain positions each demonstrating a certain direction corresponding to one of the choices of corrective optics.

The directional indicator of the viewing target may be adjusted on a display using a machine coupled with a display during a visual acuity measurement of a test subject.

The method may include determining the visual acuity of the test subject based on choices received during the visual acuity measurement using a calculator or look-up table, or both.

To prevent accommodation, the viewing target may be displayed for 0.4 seconds or less through a first corrective optic having more minus sphere than a second corrective optic to be displayed of the at least two choices of corrective optics. The viewing target may be displayed through the second corrective optic for longer than through the first corrective optic, after which the display of the first and second corrective optics may be repeated one or more times during the visual acuity measurement.

A method of self-guided refraction testing is also provided, including providing a directional indicator in a viewing target. At least two choices of corrective optics are presented from a refraction unit to a test subject while looking at the viewing target. The presenting of each of the optics is synchronized to one of the directions suggested by the directional indicator. A directional choice is received from the test subject. The directional choice of the test subject is applied in selecting a next move of the refraction procedure.

The method may include communicating the directional choice of the test subject to control a next move in presenting corrective optics to the test subject. The communicating of the test subject's directional choice may include, but is not limited to, use of a computer program, use of electronics, an electronic device and/or electronic circuits, use of a remote control unit using radio frequencies or infrared rays, or use of hard wiring connections, or combinations of the above. The test subject may perform the self-guided refraction testing without human assistance. Furthermore, the computer program may provide voice guidance to the test subject, and/or may receive voice inputs from the test subject.

The method may include receiving a further directional choice of the test subject between a different set of corrective optics in refining an optimal end point of refraction. The further directional choice of the test subject may include a reverse direction than a previous answer. A search step size may be reduced before executing a corresponding directional move.

A self-guided refraction device is also provided including an adjustable optical system, a display for presenting a viewing target including an adjustable directional indicator disposed along an optical path such as to be viewable through the adjustable optical system by a test subject, a computer coupled with the display and configured to synchronize adjustment to the corrective optics and directional indicator based on inputs received from the test subject, and one or more non-transitory computer-readable media having code embedded therein for programming the computer to control any of the methods described herein.

A method of refracting a test subject is also provided that includes choosing a starting point, and presenting a viewing target. A search step size is determined, as is a bracketing step size. The bracketing step size is equal to or greater than the search step size. A center position is located that is at least two times the search step size from the starting point. A test subject is presented with at least two choices of corrective optics. The two choices are at center position plus bracketing step, and at center position minus bracketing step. One of the choices is closer to the optimal end point than the other choice. The method includes receiving from test subject an indication of which presentation is better in quality of image of the viewing target. A time between the presenting and the receiving is recorded. The method includes moving to a new center position by one search step towards the optimal end point. The method repeats these steps confirming that the time required to make a decision continues to increase, until the test subject can no longer tell which of the two choices is better in image quality.

A method of refraction suppressing an accommodative response during a visual acuity measurement is also provided. The method involves controlling duration of presentation of two choices of corrective optics. The duration of presentation of the more minus sphere power is set to be less than 0.4 seconds. The duration of presentation of the less minus sphere power may be set to more than 0.4 seconds.

One or more non-transitory computer-readable media having code embedded therein for programming one or more processors to perform any of the methods described herein.

A refraction device is also provided for determining a visual acuity and providing corrective optics for a test subject. The device includes an adjustable optical system, a computer, and a display including an adjustable viewing target disposed along an optical path such as to be viewable through the adjustable optical system by a test subject. The computer is programmed to perform or assist in the performance of any of the methods described herein.

Figure 1A:
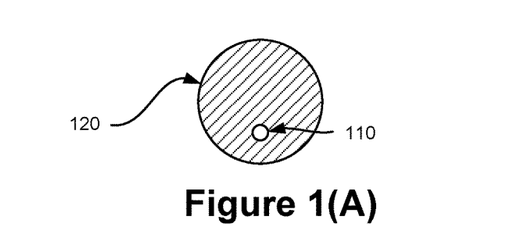
FIGS. 1(A) and 1(B) schematically illustrate a directional indicator in accordance with certain embodiments.
Figure 1B:
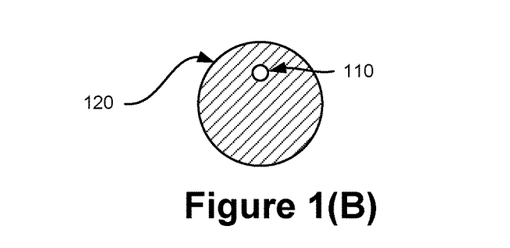

Several embodiments are described that provide refraction tests that are intuitive, and may be administered with minimum teaching or learning in the sense that they generally do not require complicated logic or memorization. A directional indicator is generally provided in a viewing target. An example of a directional indicator is schematically illustrated at FIGS. 1(A) and 1(B). The directional indicator of FIGS. 1(A) and 1(B) includes a relatively light (e.g., white) dot 110, within a dark (e.g., black or blue) circular area 120. The dot 110 may be distinguishable from the area 120 in many ways, including having different colors or grayscale values, or the dot 110, which may have any arbitrary shape, may protrude from the area 120 which may also have any arbitrary shape. The area 120 is optional, as the "dot" 110 may have a directional shape, e.g., that is rotationally dependent such as an arrow or any rotationally asymmetric shape, character, symbol, polygon, indicator, letter, number, curved line or shape, or other distinguishable object.

In the example of FIG. 1(A), the white dot 110 is at a "top" position, while in FIG. 1(B) the white dot 110 is at a "bottom" position. The timing of the location of the white dot, at either the top or bottom position, is dynamically linked to the presentation of the lenses, or the optics, as the test subject is looking at the viewing target through these optics. In another example, an arrow may point up corresponding to the position of the white dot in FIG. 1(A) or the arrow may point down corresponding to the position of the white dot in FIG. 1(B), or the arrow may point right and left, or Superman may be flying up or down, or any other directionally-definitive combination.

Figure 2:
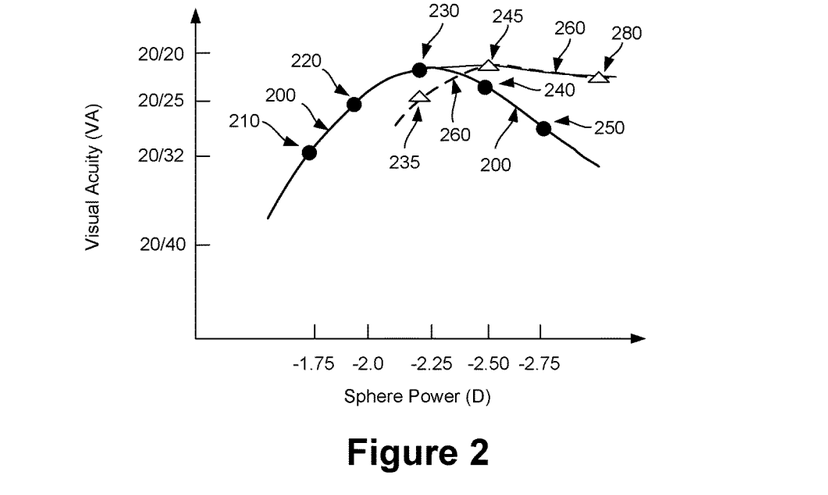
FIG. 2 includes illustrative plots of visual acuity versus sphere power.

Most of a refraction test involves a search for an optimal corrective lens. Therefore, in the process of a search, a quality of vision may become improved, stay the same or become worse. An example is illustrated in FIG. 2. The curve represents change of sphere power in the x axis, and the corresponding visual acuity (VA) level in the y-axis. In this example, the test subject has the best VA of 20/20 at −2.25 D. In this example, the patient is 70 years old and has zero accommodation power. The lenses may be motor driven, and a desired sphere power may be presented to the test subject on demand. That is, once the test subject indicates better one or better two using an input device in a way suggested by the directional indicator associated with the choice of the test subject, then an advantageous refraction apparatus in accordance with certain embodiments automatically provides the next choice based on the input received from the test subject. Using the example of FIGS. 1(A) and 1(B), if the first choice is associated with FIG. 1(A) and the second choice with FIG. 1(B), then the patient may move a joystick up to select the first choice or down to select the second choice, or the patient may click a mouse with the cursor over an upper object for the first choice or a lower object for the second choice.

Since the refraction process described here is intuitive in nature, it can be performed by a test subject alone, or it can be conducted by a third party person. A computer program may provide voice guidance throughout the refraction process. It may also perform a communication function, receiving input from the test subject, which is derived from its directional choice, sending that to an optical system, adjusting the directional indicator and synchronously presenting corrective optics for a test subject to look through while looking at the viewing target.

Referring to FIG. 2, in an example refraction process, a −1.75 D lens may be first presented along the line of sight of the test subject. This may provide a VA of 20/32 as illustrated at 210 of FIG. 2. The next presentation 220 in this example is a −2.0 D lens that is provided. In accordance with certain embodiments, the lens 210 at −1.75 D is presented at the same time as a directional indicator, e.g., such as that of FIG. 1(A), where the white dot 110 is displayed in the "Top" position within the disk 120. The presentation duration may be chosen from 0.3 seconds to 1.5 seconds, or even 5 seconds or more. In certain embodiments described in more detail below, the more negative sphere is presented for 0.4 seconds or less to avoid accommodation, while the more positive sphere may be presented longer. Next, a lens at 220 in FIG. 2, at −2.0 D, is presented. The directional indicator of FIG. 1(B) is presented at the same time as this second lens choice, i.e., the white dot 110 moves to the "bottom" position within the disk 120 (or the arrow flips to point down, etc.). That is, the directional indicator changes from FIG. 1(A) to FIG. 1(B) synchronously with the movement of lens presentations from −1.75 D at 210 in FIG. 2 to −2.0 D at 220.

The presentations 210 and 220 may be repeated automatically until the test subject makes a choice answer, e.g., in this case the "bottom". An input device, such as a mouse, or a joy stick is provided to the test subject. Sound may also be used such as a computer program trained to distinguish "the first one" from "the second one" when the test subject speaks his or her choice. The test instruction may be quite simple, e.g., if the quality of the image is better when the dot is at the top position, move the joy stick towards the "top", or roll the mouse wheel up by one click, or push the joy stick away from the test subject or speaks certain words that a microphone coupled to a machine can pick up. Likewise, if the image when the dot is at the bottom is more sharp and focused, move the mouse wheel or the joy stick towards "bottom", or towards the test subject. These instructions are simple and intuitive as intended for broad application. A trigger button at the end of a joy stick may be used as an indication when the two presented images are close to being equal or there may be a third "equal" choice otherwise provided. In the case of using a mouse, an "equal" may be indicated by pushing both the left and right clicks at the same time or just the right click or by putting the cursor neither over the first or second choices and clicking.

In the example of the mouse wheel, after one click down, indicating that the test subject prefers 220 over 210 in FIG. 2, a computer program may automatically instruct a processor to present 220 and 230 as the next two choices, e.g., with more positive power having the directional indicator of FIG. 1(A), e.g., the white dot at the top position, again. In this case, 230 at −2.25 D of FIG. 2 provides the best vision for the test subject as illustrated. The exemplary mouse wheel input device is moved one click down indicating image at 230 is better than 220 for this test subject. In the next presentation 230 may be presented against 240. This time the test subject should pick 230 over 240, e.g., by rolling the mouse wheel upward, indicating that he or she prefers the image when the dot is at the top. The computer is programmed to recognize that the mouse direction has been reversed, and concludes that an optimal acuity end point has been reached at 230.

In this example, no human operator needed to once ask "better one or better two?" nor does an operator need to present choices repeatedly to seek an answer from the test subject. The entire sphere lens search may be performed entirely self guided by the test subject with the assistance of an advantageously configured machine. Another aspect of a self-guided refraction procedure in accordance with certain embodiments is that test subject may provide input or answers to the refraction computer program, without taking his or her eyes off the test target.

Viewing Target

Figure 3A:
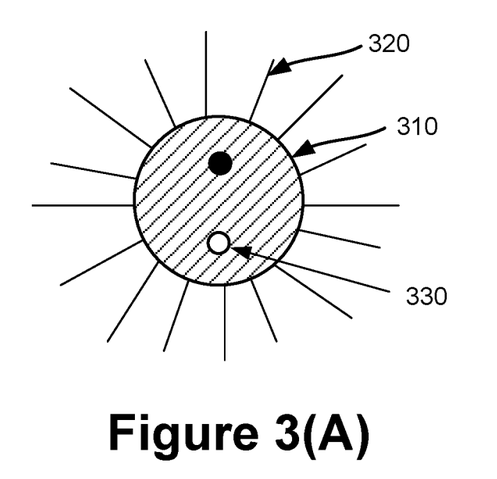
FIG. 3(A) schematically illustrates a viewing target for a visual acuity measurement including a directional indicator in accordance with certain embodiments.
Figure 3B:
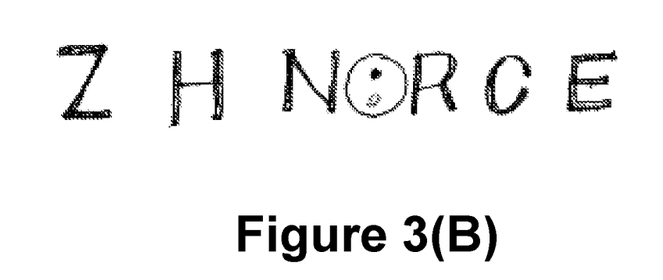
FIG. 3(B) illustrates a viewing target including a directional indicator in accordance with certain embodiments.

In FIG. 3 (A), a directional indicator in accordance with certain embodiments is modified from that illustrated at FIGS. 1(A) and 1(B) to include a series of thin lines emanating from the disk 110 (or other arbitrary shape). A detailed description of such a viewing target is provided in contemporaneously-filed patent application by Shui Lai, entitled "Effective Acuity and Refraction Targets" which is incorporated by reference. Such target has higher sensitivity than a typical Snellen letter eye chart, and has other benefits including reducing a likelihood of over-minusing. Another refraction target is illustrated at FIG. 3(B), where a row of Snellen letters are presented. Disposed in the middle of the row of letter is the directional indicator of FIGS. 1(A) and 1(B). The exact location of the directional indicator is not a limiting factor, as it can be placed anywhere within the viewing angle of the test subject. However, it may be easier for the test subject if it is placed in the midst of a viewing target, as in the examples of FIGS. 3(A) and 3(B). In one embodiment, the letter size displayed in FIG. 3(B) may be adjustable electronically or manually.

Adjustable Optical System

An instrument may be used that is capable of presenting and changing to a specified lens power via motor control. One such instrument is described in a patent by the same inventor, Shui Lai, which is U.S. Pat. No. 7,726,811, entitled "Subjective Refraction Using Continuously Variable Zernike Wave Plates" and is incorporated by reference.

In such an instrument, the spherical power may be adjustable by moving a lens in a spherical adjustable assembly, or SAS. The lens may be moved in a linear dimension, e.g., riding on low friction rails. The latency time may be about 50 milliseconds for a 0.5 diopter movement or somewhere between 1-10 ms and 100-500 ms. The astigmatism power may also be adjustable by counter-rotating a pair of pure astigmatism optic plates. The full power range can be scanned through a 45 degree rotation. The latency of the astigmatism for a 0.5 diopter change may also be in a range around 50 milliseconds such as between 1 ma and 100-500 ms. The response time of such device can be improved by using lighter materials and smaller optics, and somewhat longer response times may be tolerated. That is, neither the 50 millisecond response time nor the described ranges are limiting factors.

Other methods of making lens power changes can be adapted in further embodiments, without limitation. For example, a fluid lens such those described in US patents U.S. Pat. Nos. 4,477,158, and 4,953,956 can also be used here, and as such these patents are incorporated by reference. Since the lens power may be achieved through injecting or removing fluid in a confined volume, these have the advantage of having fewer or no moving mechanical parts. Piezoelectric actuators can be used in the pumping mechanism to improve the response time of the fluid lens power change.

Another example of a fast power acting lens is a liquid crystal wave plate device, such as those described in U.S. Pat. No. 4,601,545, which is incorporated by reference. By changing the optical path difference of the wave plate in a manner simulating that of a spherical power lens, one may make such liquid crystal device to behave just like a lens. A drawback of liquid crystal lens however is its limited power range. Since the power difference in the two presentations is about 0.5 D, liquid crystal lenses are well suited to be used in certain embodiments to provide a power difference. In the example of FIG. 2, a liquid crystal lens may be added to a traditional phoropter, or any suitable device, including one in U.S. Pat. No. 7,699,471 by Shui Lai, which is incorporated by reference. The phoropter lens power may be set in the middle between the presented powers. For example, if one were to present 220 and 230 of FIG. 2, then the phoropter could be set in the middle, or at −2.125 D. The liquid crystal lenses can provide the added difference of 0.125 D at the top position, and -0.125 D at the bottom position.

Controlling Accommodative Response in a Refraction Test

In certain embodiments the time duration of the presentation of a refractive target to a patient under examination is controlled to curtail accommodative response. The dynamic nature of the target presentations may be manipulated in such a way as to produce desirable effects, such as eliminating over-minus, and arriving at more accurate end points quickly.

A test subject who is a young person will have accommodative power in his or her eye. A viewing target such as that illustrated at FIGS. 1(A) to 1(B), or the modified Snellen eye chart of FIG. 3(B), for example, may be presented to the test subject. In this case, if the presentations of 230 and 240 in FIG. 2 are both one second or longer, then due to the accommodative response of this test subject, the quality of the image at −2.5 D now may look the same as at 230 following the accommodation curve 260, or having almost the same acuity at 245 or 280, compared with the changes presented at 240 or 250 not impaired by accommodation. That is, at 245 and 280 an elevated acuity level is the result of accommodation into an over-minus region. Worse than that, once the accommodative response is triggered, the young test subject may even say that 245 is more focused than 235, where the acuity actually appears to have dropped from 230 on the real curve 200 to 235 on the accommodated curve 260, due to the extra plus power at the test subject's natural lens.

Recognizing the existence of accommodative response, a process in accordance with certain embodiments controls it. An accommodative response takes about 0.3 to 0.4 seconds for the natural lens to add the extra plus power to make over-minus vision appear to be sharp and focused. Thus, a dynamic presentation method may be used which limits the presentation time period to be equal to or less than the accommodative response time. For example, when −2.5 D at 245 of FIG. 2 is presented as the more minus power choice when the other choice is −2.25 D at 230, then the −2.5 D power is provided for 0.4 second or less. Used as an example, the presentation at −2.5 D may be set to 0.4 seconds, 0.3 seconds, 0.2 seconds or 0.1 second, and that of −2.25 D may be set higher, e.g., to 1 second. When the two lenses power are presented repeatedly at the respective time durations, e.g., 1 second and 0.3 seconds, the dot of FIGS. 1(A) and 1(B) jumps between the top and bottom positions (or an arrow flips up and down, etc.), synchronized with the presentation of changing optics.

The presentation period of the more positive sphere power may be intentionally set at a time much longer than the accommodative response time of 0.4 or 0.3 seconds, or it may be the same or similar duration. The viewing time may favor the more positive power presentation of −2.25 D. Therefore, even for this test subject, −2.5 D presentation remains to be at the 240 acuity level of FIG. 2, and not at 245 with accommodative response. In this way, reduction or elimination of over-minusing is provided using a dynamically linked viewing target with a proper choice of presentation time, and synchronization between the target and the optics. In this case the test subject identifies 230 at −2.25 D as being more focused than 240 at −2.5 D. The lens power at 230, at −2.25 D is then determined to be the optimal power for this test subject. Over-minusing conditions have been prevented in this example.

The sphere powers used in the example above are also not limiting factors. The test subject may have other values as his or her final optimal sphere power not affecting the benefits and working principles of the advantageous process. Also, neither the incremental power change of 0.25 D, nor the acuity level of the test subject, as illustrated in the y-axis of FIG. 2 are limiting factors.

The lens power modulator can be achieved using a liquid crystal lens, a fluid lens (or liquid cell lens), or a continuously adjustable phoropter as in the instrument described for example in the earlier-cited patents by Shui Lai.

In FIGS. 1(A), 1(B), 3(A) and 3(B), the circular area 120 with dot 110 are used as non-limiting examples, and use of the top and bottom positions in that example indicator is itself an example.

That is, the dot positions may be right and left, instead of top and bottom. In such case, the accompanying instructions might include "move the joy stick to the right if the image appears sharper and more focused when the dot is on the right, and move the joy stick to the left, if the image appears sharper when the dot is at the left position." In this case, the mouse wheel may not work as well, since the test subject has to remember, left is to move the mouse wheel up one click, left to roll the mouse wheel down one click, but user-preferences may be selected. Instead of jumping dots, one could use an arrow that changes pointing directions up and down, either by itself or within the circular area 120 or protruding out of the circular area 120. An up arrow would suggest to move the mouse wheel up one click, and a down arrow to move the mouse wheel down one click, etc.

One advantage of certain embodiments is that the directional indicator may be relatively small and can be seen centrally without rolling the eye ball, or its gaze angle. Likewise, when a letter in FIG. 3(B) is being looked at, the jumping dot in the circular area is within the "peripheral vision" of the stare. It is advantageous to provide a quick determination whether the quality of the vision is better or worse at one of the two dot positions, without taking the eye off the letter the test subject is staring at.

Bracketing Method to Find the Optimal End Point

The above-described embodiments involved finding a refraction end point in searching for an optimal sphere power by locating a best quality image as an optimal end point, or at a sharpest focus point. Another method is to find the best "bracketed" locations as the end point. In this method, slightly blurred images are provided and the test subject is asked to compare his or her degree of blurriness. At the end point, the quality of image is not at it sharpest focus, but rather, the two presented views are close to being equally blurred.

This method is particularly advantageous for finding an optimal end point where there is no hazard involving accommodative response when a presentation is at a position after passing the optimal point, similar to the over-minusing conditions in finding the optimal sphere value. Therefore, this method is particularly advantageous when searching for axis angle and the power of the optimal cylinder.

Figure 4:
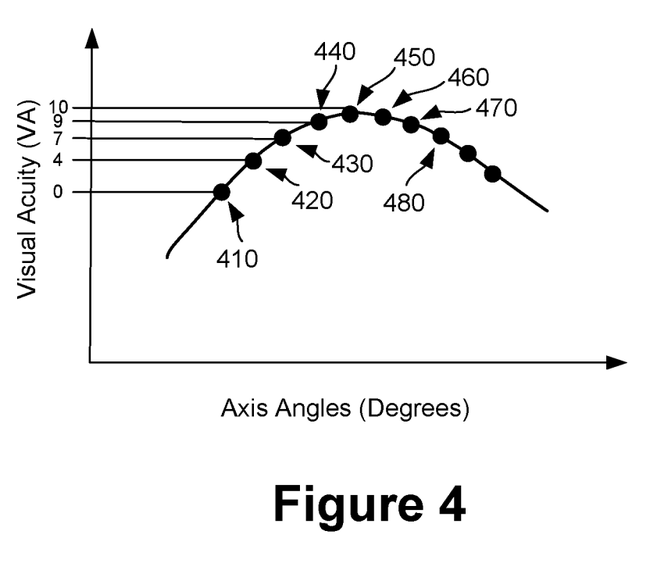
FIG. 4 include a plot of visual acuity versus axis angle.

We illustrate this method in FIG. 4, in a search of an optimal axis angle at a given cylinder power. Like FIG. 2, the acuity level is in the Y axis, and in this case, the axis angle is in the X axis, unlike FIG. 2 which has the sphere power in the x-axis. A relation curve is shown FIG. 4 to illustrate how acuity may vary with the axis angles. Each of the points 410, 420, . . . , to 480 may be separated by, e.g., 5 degrees axis angle from each neighboring point. The difference in acuity level is recognized herein as not being the same as the axis angle varies across the curve from 410 to 420, as compared to from 430 to 440. In fact the acuity level difference between 410 and 420 may be greater by a factor of two as these neighboring points are farther away from the optimal region than those at points 430, 440, and 450. From here on, we use the definition of VA(410), to mean the visual acuity level of the test subject when the optics are presented to him or her at axis angle position 410 in FIG. 4. For example, VA(410)–VA(420) is 1.5× to 2× of VA(430)–VA(440). Likewise comparisons can be made between the VA(450)–VA(440), and the previous two sets of neighboring points, and so on. It is recognized herein that it is not effective to find an optimal end point by comparing the nearest neighbor points. Instead, a larger bracket size may be advantageously used in accordance with certain embodiments, while maintaining a small nearest neighbor step size in the end point search.

As an illustrative example, if one starts at point 430 in FIG. 4, two choices may be presented at 410 and 450. If a directional indicator target in accordance with certain embodiments is used, then the viewing target may be viewed with axis angle 410 and FIG. 1(A), while the acis angle 450 may be viewed with the indicator FIG. 1(B). Whether or not a directional indicator is used in this embodiment, the test subject is asked to determine of 410 and 450 provides a sharper image. The sensitivity may be increased by a factor of 8, for example, as compared to presenting point 440 and point 450. That is, a test subject can more easily pick 450 by moving an input device per bottom indicator of FIG. 1(B) to indicate that the viewing target is sharper and more focused than the 410 choice. In this case, the center point is the 430, and the brackets are 2 times the nearest neighbor step size.

Since the test subject determined at this step that the "bottom" (FIG. 1(B)) choice 450 is more focused, he or she may roll the mouse wheel down by one click, or otherwise indicate the choice of 450 over 410. The new center position would be moved towards 450 to be now 440, for example, for a next step in the test. This move of one nearest neighbor step may be referred to as a mouse move step size. By this definition the brackets are +/−2 mouse move steps, centering at 440, in this case. The test subject will now compare a viewing target at 420 to one at 460. Again, it should be an easy choice for the test subject who would answer "bottom" choice or that suggested by directional indicator of FIG. 1(B).

Then next, point 430 is compared to 470, and the center point is at 450, the supposed optimal point in this example. Now the acuity level of these points should be about equal, and test subject might say or indicate, "Equal", such that the optimal end point is obtained.

Timing for Test Subject's Response

This test is easier when the center point is farther from the optimal end point. For example, in the last example, when the test started at 430, the difference of image quality between 410 and 450 which is the presumed optimal end point, is very obvious to the test subject. As an aside, one may use an arbitrary scale on the Visual Acuity (VA) axis, and shift the zero to VA(410) a illustrated in FIG. 4. Relative values may be assigned to the corresponding points for VA(420), VA(430), etc as illustrated. The point is that the exact value for each of the VA points is not critical, but rather the goal is to determine changes of the VA values which become smaller and smaller until the center point becomes the optimal end point, which is this example is at 450 and VA=10 (a.u.).

Now, at the start of this example test, the center point was at 430, and the difference of image quality, VA(450)–VA(410)=10 units as shown in FIG. 4. Next the center point is moved to 440, the image quality in acuity is VA(460)–VA(420)=9−4=5, or half the difference of the previous step. The next mouse click moves the center position of the bracketing to 450, now the difference in image quality is zero. It is recognized herein that the test subject would find it easier to answer when the center point is at 430, than when at 440, and would find it very hard to tell which of the two is actually better at 450. This "degree of easiness" of choice is used to find the optimal end point, i.e., when the choice is toughest then the center point is the optimal endpoint.

A self-guided refraction test machine, e.g., a computer or other processor-based device, may be used to monitor a time duration for the test subject to give an answer after each new center position. For example, the test subject may only need 1 to 2 jumping dot periods to answer when the center position is at 430, and may need 3 to 4 jumping dot periods to answer when the center is at 440, and he or she may take up to 5 periods or more to decide that he or she actually cannot tell whether the top or the bottom is more focused when the center is at 450. Also, in a self guided refraction test in accordance with certain embodiments, the number presentation periods may be recorded. The test may also take into account that an optimal end point is approached when the test subject is taking increasingly longer times to provide answers. If an answer cannot obtained after 10 periods, for example, the program can actually decide to pick that as an "Equal" for the test subject.

Auto Refinement on Reversing

If in the last example, the optimal end point is not at 450, but rather somewhere between 440 and 450, then the test subject may say "the top position is slightly more focused." Now we have a reversing situation, namely when the center position was at 440, patient asked for "bottom", but when the optics were moved to 450, he asked for "top". The computer program can repeat itself between these two central positions and run itself into a repeat loop. An auto refinement algorithm may be provided wherein when a reversing situation occurs, the mouse move step size is reduced by a factor of 2, before it executes a command to move a step towards "top". Now a move towards "top," effectively moves the center position to the middle of 440 and 450. If the test subject confirms this is the optimal end point, and answers "Equal", then the angle search in this case is finished. However, if further reversing occurs, auto refinement can continue to sub-divide the mouse move step size by a factor of 2 in each reversing until a final end point is reached.

The search step may be in the increments of the nearest neighbor point step, while the brackets may be at two times the neighboring point distance. The end results may be increased sensitivity in the test, and more certainty in the finding the end point, without compromising search step accuracy.

For a search over a larger region of angles, one may use a speedy search. The mouse steps and the bracketing steps may be increased by a factor of 2, for example. The speedy search may be increased by a factor of two, but the accuracy may be compromised with the rougher search step size.

However, once a rough optimal end point has been established, the mouse step may be reduced as well as the bracketing step by, e.g., a factor of 2, or may be set forth and described in the auto refinement procedures. A general approach may be to find the general vicinity near the optimal end point using quick and larger steps, and then to refine step size to fine tune to the approximately exact end point.

The bracketing method is also applicable for a search of optimal cylinder, or astigmatism power. One would have to replace the axis angle label in the X axis in FIG. 4 with an astigmatism power, rather than axis angles, and then the rest of the methods, including bracketing, timing of answers, and auto refinement, apply.

Example Self Guiding Refraction Procedure

Figure 5:
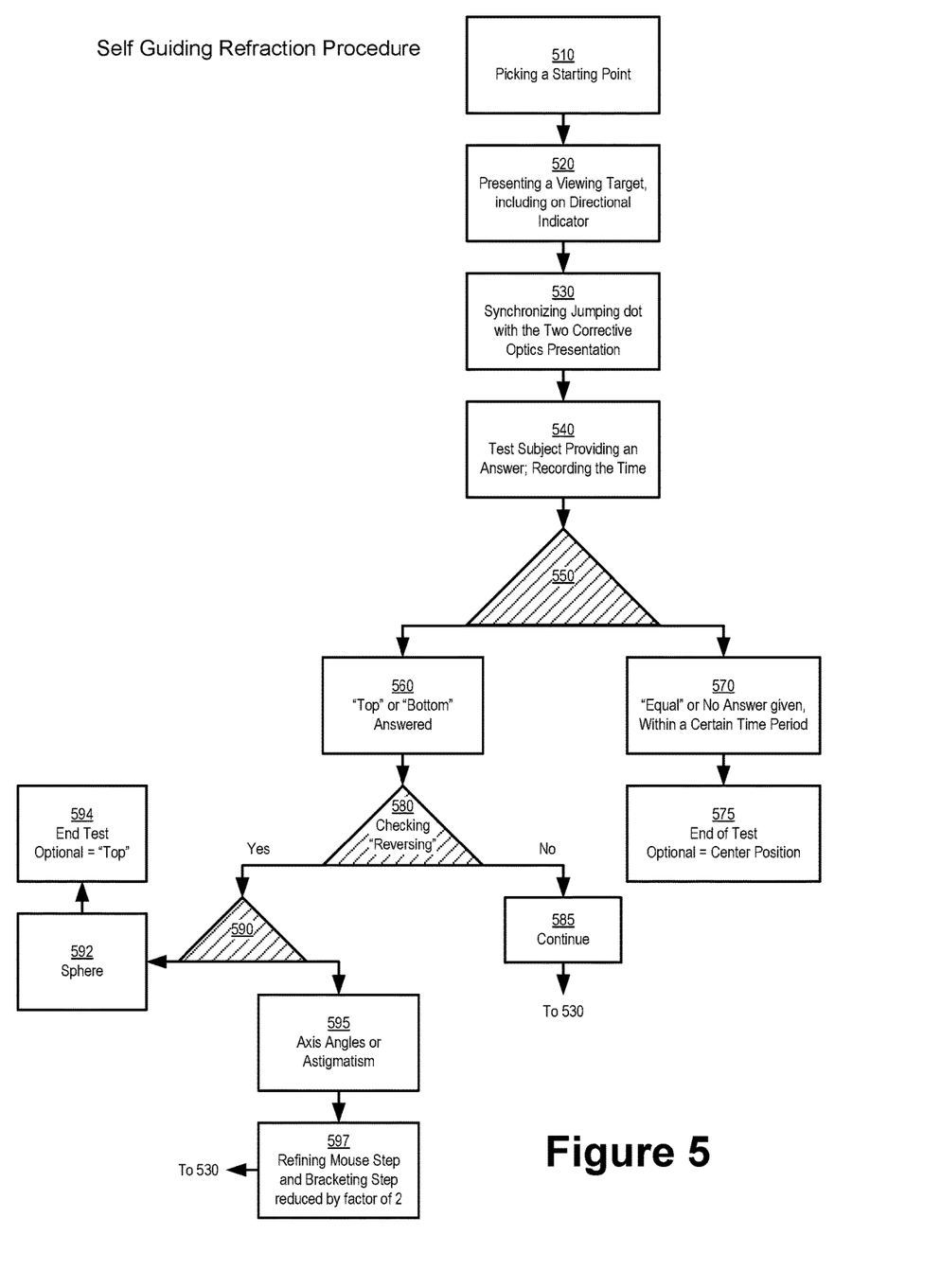
FIG. 5 illustrates a process flow in accordance with certain embodiments.

FIG. 5 illustrates a self guided refraction procedure. At box 510, the start of refraction, a starting point is chosen. The starting point can be selected with the aid of an autorefractor, wavefront aberrometers, or a retinoscope, or a previous measurement, or an starting arbitrary point may be used. These values may be either manually or electronically populated from a electronic medical record software.

Next, at box 520, an operator may choose to start finding a sphere, axis angle, or the power of a cylinder end point. The flow chart may be applied to any or all of the three cases. A viewing target including a directional indicator may be selected or assigned, and used, such as illustrated in the examples of FIGS. 1(A), 1(B), 3(A) and/or 3(B), or an arrow that flips, or otherwise.

At box 530, a white dot is moving synchronously in a directional indicator, e.g., as illustrated at FIGS. 1(A) and 1(B). Two presentations (or dual presentations) may be used, where optics settings may switch between +/− bracketing values from a center position. They can be two axis angles of fixed astigmatism optics, or two sphere values, or two astigmatism diopter settings.

At box 540, a test subject may provide an answer after a presentation has been repeated a number of times. The time lapse may be recorded from the start of optics presentations to the test subject to the time of receipt of an answer/choice by the test subject.

At box 550, if the answer is either a "Top" (FIG. 1(A) or similar) or a "Bottom" (FIG. 1(B) or similar), then the process can branch at 550 to box 560. Otherwise, at box 570, when the answer at 540 is "Equal" or no answer is given for a time longer than a predetermined time, e.g., as may be fixed or adjusted from previous presentations, then the test may be ended at box 575, and the optimal end point is the center position between the two choices in the final presentation, or at the middle between the top and bottom presentation values.

From box 560 however, there is another query at 580 to check whether the answer is in the reversed direction of the previous answered direction. Of course, if this is the first answer, or it is not a reversing answer, then the test continues to 585, then moves to the next center position and back at 530 the optics are presented at a +/− bracketing values about the new center value.

If it is a reversing from box 580, then the next query at 590 is to determine if the measurement is for sphere value 592, or if it is for axis angle or astigmatism at box 595. If it is for sphere, then at box 594 the test is finished and the optimal end point for the sphere is the value at the "Top" optics position.

If reversing occurs with axis angles or astigmatism power, then from box 595, the process moves on to box 597 where a refinement of the mouse move step size is made, and to the bracketing step size, e.g., both may be reduced by a factor of 2. A mouse click execution input may be received in accordance with the patient response from Box 560, i.e., top or bottom. Then, the process continues back to box 530 at the new center value, and new bracketing values, and continues with the flow chart.

The described embodiments are merely illustrative and the invention is not limited to the specifically-described examples. Instead, the invention is set forth in the claims and includes structural and functional equivalents thereof.

What is claim is:

1. A self-guided refraction method, comprising:
    (a) providing a viewing target and an optical system including adjustable corrective optics for a test subject to view the viewing target;
    (b) presenting to the test subject at least two choices of adjustable directional indicators at the viewing target;
    (c) providing at least two configurations of corrective optics, wherein a first directional indicator is synchronously linked to a first configuration of the corrective optics, and a second directional indicator is synchronously linked to a second configuration of corrective optics;
    (d) receiving an audio voice indication from the test subject from a voice activated device, microphone, or other audio voice receiver a choice among the at least two choices of directional indicators, thereby indicating a choice among the at least two choices of corrective optics;
    (e) adjusting the corrective optics in a direction chosen by the test subject corresponding to the test subject's choice of the directional indictor, and
    (f) wherein at least one of said choices of directional indicators comprises a first object that is embedded within a second object on a display, or that is movable between at least two positions within said second object on said display, or that is adjustable between at least two configurations, orientations or positions, or combinations thereof, linked synchronously to at least two choices of corrected optics presented to the test subject.

2. The method claim 1, further comprising:
    (i) determining a difference between the first configuration and second configuration of corrective optics in accordance with the test subject's visual acuity, and
    (ii) adjustably setting a bracketing step size in accordance with the determined difference between the first and second corrective optics.

3. The method of claim 2, further comprising moving the center point between the first and second configurations of the corrective optics by a search step size.

4. The method claim 3, wherein the moving of the center point comprises moving the center point in a direction according to the choice made by the test subject among the at least two choices of directional indictors.

5. The method claim 2, further comprising positioning the first configuration and second configuration of corrective optics in a bracket around a center point between the first configuration and the second configuration of corrective optics.

6. The method of claim 5, further comprising moving the center point between the first and second configurations of the corrective optics by a search step size.

7. The method claim 6, wherein the moving of the center point comprises moving the center point in a direction according to the choice made by the test subject among the at least two choices of directional indictors.

8. The method of claim 2, comprising advancing the refraction process and continuing moving the center position in the same direction according to the choice by the test subject until the test subject indicates to reverse the direction of movement of the center point.

9. The method of claim 8, comprising refining the adjusting upon said reverse of direction by the test subject, comprising:
reducing the bracketing step size to a smaller value by a multiplier factor, wherein the multiplier factor is less than 1, and
continuing the refraction test until a prescriptive recommendation is determined.

10. The method of claim 1, comprising repeating (d) and (e) until the test subject indicates the quality of the images of the target appears close to being equal among the at least two choices of directional indicator, or until a prescriptive recommendation is determined, or both.

11. The method of claim 1, wherein the adjusting of the corrective optics comprises adjusting one or more of the following elements:
(a) A trial lens set;
(b) A manual phoropter;
(c) An auto phoropter;
(d) A spherical adjustable assembly;
(e) Astigmatism optic plates;
(f) Liquid lenses;
(g) Liquid crystal lenses;
(h) Adaptive optics or deformable mirrors;
(i) Combinations thereof.

12. The method of claim 1, wherein the providing of a viewing target includes showing an image of the viewing target in an electronic display, a monitor, or other display media.

13. The method of claim 1, wherein the presenting of at least two adjustable directional indicators comprises presenting one or more of the following:
(a) at least one dot, or
(b) one or more lines, or one or more curved lines, or one or more bars, or
(c) one or more arrows or other symbols, alphabetic characters, or numbers, or
(d) one or more shaped objects, a circular, semi-circular, oval, square, rectangle, hexagon, octagon, or polygon, or
(e) combinations thereof.

14. The method of claim of 13, wherein the at least two adjustable directional indicators comprise black characters on a white background or white characters on a black background.

15. The method of claim 14, further comprising changing a contrast of the at least two directional indicators by adjusting the black or white, or both, to one or more different shades of grey.

16. The method of claim 1, further comprising providing computer-generated voice guidance to the test subject.

17. The method of claim 1, wherein the adjusting the corrective optics comprises running a software program that programs one or more processors to control the adjusting of the corrective optics.

18. The method of claim 17, further comprising moving the center point between the first and second configurations of the corrective optics by a search step size.

19. The method of claim 18, wherein the moving of the center point comprises moving the center point in a direction according to the choice made by the test subject among the at least two choices of directional indictors.

20. The method of claim 1, comprising controlling the accommodative response of the test subject, including presenting the viewing target (i) for a first duration equal or less than the accommodative response time of the test subject through a first corrective optics having more minus sphere value, and (ii) for a second duration longer than the accommodative response time for a second corrective optics having a more plus sphere value than that of the first corrective optics.

21. The method of claim 1, comprising controlling a duration of presenting corrective optics, and a duration of presenting directional indicators.

22. The method of claim 1, comprising determining a visual acuity of the test subject.

23. The method of claim 1, comprising providing a third choice of directional indicator that is synchronously linked to a third configuration of corrective optics.

24. A refraction device for determining a refraction end point and providing corrective optics for a test subject, comprising:
(a) an adjustable optical system providing corrective optics to the test subject;
(b) an adjustable viewing target disposed along an optical path such as to be viewable through the adjustable optical system by a test subject, and
(c) a voice activated device, microphone, or other audio voice receiver for receiving an audio voice indication from the test subject; and
(d) wherein at least two distinct configurations of the adjustable viewing target are linked synchronously to at least two choices of corrective optics to be presented to the test subject;
(e) wherein the adjustable viewing target comprises a directional indicator on a display, that changes synchronously between at least two objectively distinct attributive forms with the at least two choices of corrective optics, and
(f) wherein the directional indicator comprises:
i. at least one dot, or
ii. one or more lines, or one or more curved lines, or one or more bars, or
iii. one or more arrows or other symbols, alphabets, or numbers, or
iv. one or more shaped objects, a circular, semi-circular, oval, square, rectangle, hexagon, octagon, polygons, or
v. combinations thereof, and
(g) wherein said directional indicator comprises a first object that is embedded within a second object on a display, or that is movable between at least two positions within said second object on said display, or that is adjustable between at least two configurations, orientations or positions, or combinations thereof, linked synchronously to at least two choices of corrected optics presented to the test subject.

25. The refraction device of claim 24, comprising an input device configured to execute a move in a refraction process in accordance with a direction suggested by the directional indicator which is selected by the test subject, while the test subject selects between the at least two choices of corrective optics.

26. The refraction device of claim 25, wherein the executing is controlled by a communicative device, which receives a selection from the test subject, and performs a refraction process based on the selection from the test subject.

27. The refraction device of claim 26, wherein the communicative device comprises an electronic device controlled by the test subject.

28. The refraction device of claim 26, wherein the communicative device provides computer-generated voice guidance to the test subject.

29. The refraction device of claim 26, wherein the communicative device comprises said voice activated device which receives said selection from the test subject by voice response.

30. The refraction device of claim 29, wherein the voice activated device comprises:
(a) a microphone; or
(b) a computer program trained to recognize words spoken by test subject, or both.

31. The refraction device of claim 25, wherein the direction suggested by the directional indicator corresponds to a corrective optics choice for the next move of the refraction process, approaching an optimal refraction end point.

32. The refraction device of claim 24, wherein the adjustable viewing target is adjustable to at least two configurations each uniquely indicative of one of the choices of corrective optics.

33. The refraction device of claim 24, wherein the directional indicator comprises a relatively light dot inside a dark area, or vice-versa, a bar or other in-plane rotationally asymmetric polygon, an arrow, a line, or another in-plane rotationally-dependent object, or combinations thereof, and is configured to be displayed to the test subject in at least two configurations each uniquely indicative of one of the choices of corrective optics.

34. The refraction device of claim 33, wherein the directional indicator comprises a white dot inside a black area, and such that the white dot is movable to certain positions each demonstrating a certain direction corresponding to one of the choices of corrective optics.

35. The refraction device of claim 24, further comprising a machine coupled with a display displaying the viewing target, and configured to adjust the viewing target during a visual acuity measurement of a test subject.

36. The refraction device of claim 35, further comprising a calculator or look-up table, or both, for determining the visual acuity of the test subject based on the visual acuity measurement.

37. The refraction device of claim 24, wherein to prevent accommodation the device is configured to display for a duration equal or less than the accommodation response time of the test subject, wherein a first corrective optics has more minus sphere than a second corrective optics among the at least two choices of corrective optics.

38. The refraction device of claim 37, wherein the second corrective optics is configured to be displayed after the first corrective optics for longer time than that of the first corrective optics, after which the display of the first and second corrective optics is repeated one or more times.

39. The refraction device of claim 24, wherein the corrective optics comprise:
(a) a trial lens set;
(b) a manual phoropter;
(c) an auto phoropter;
(d) a spherical adjustable assembly;
(e) astigmatism optics plates;
(f) liquid lenses;
(g) liquid crystal lenses; or
(h) adaptive optics; or
(i) combinations thereof.

* * * * *